(12) United States Patent
Viker

(10) Patent No.: US 8,496,667 B2
(45) Date of Patent: Jul. 30, 2013

(54) DEPLOYABLE SEGMENTED TLIF DEVICE

(75) Inventor: Thomas O. Viker, Arden Hills, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 13/236,104

(22) Filed: Sep. 19, 2011

(65) Prior Publication Data

US 2012/0004731 A1 Jan. 5, 2012

Related U.S. Application Data

(63) Continuation of application No. 11/683,756, filed on Mar. 8, 2007, now Pat. No. 8,021,429.

(51) Int. Cl.
*A61B 17/88* (2006.01)
*A61F 2/44* (2006.01)
*A61F 2/46* (2006.01)

(52) U.S. Cl.
USPC .......................... 606/99; 606/914; 623/17.16

(58) Field of Classification Search
USPC ................ 606/99, 100, 103, 263; 623/13.13, 623/17.11–17.16
See application file for complete search history.

(56) References Cited

U.S. PATENT DOCUMENTS

| | | | |
|---|---|---|---|
| 5,207,694 A | 5/1993 | Broome | |
| 5,370,646 A * | 12/1994 | Reese et al. | 606/324 |
| 5,529,225 A | 6/1996 | Chang | |
| 5,553,754 A | 9/1996 | Dentler | |
| 5,704,943 A * | 1/1998 | Yoon et al. | 606/139 |
| 5,716,416 A | 2/1998 | Lin | |
| 6,039,761 A | 3/2000 | Li et al. | |
| 6,193,757 B1 | 2/2001 | Foley et al. | |
| 6,387,130 B1 | 5/2002 | Stone et al. | |
| 6,395,031 B1 | 5/2002 | Foley et al. | |
| 6,613,090 B2 | 9/2003 | Fuss et al. | |
| 6,893,466 B2 | 5/2005 | Trieu | |
| 7,004,945 B2 | 2/2006 | Boyd et al. | |
| 7,018,413 B2 | 3/2006 | Kruger | |
| 7,594,888 B2 * | 9/2009 | Raymond et al. | 600/219 |
| 7,846,208 B2 * | 12/2010 | Cauthen et al. | 623/17.16 |
| 7,985,257 B2 * | 7/2011 | Cauthen et al. | 623/17.11 |

(Continued)

FOREIGN PATENT DOCUMENTS

DE 19710392 C1 7/1999
DE 20314708 U1 12/2003

(Continued)

*Primary Examiner* — Michael T Schaper
(74) *Attorney, Agent, or Firm* — Seager, Tufte & Wickhem, LLC

(57) ABSTRACT

A segmented intervertebral body fusion support includes a plurality of segments, the segments including an initial segment, a final segment and at least one intermediate segment. The intermediate segment has a generally trapezoidal configuration and the initial and final segments include tapered side walls providing triangular gaps between adjacent segments. A draw wire is fixed to the first segment and passes through the remaining segments. By pulling the draw wire relative to the segments, the segments are drawn together in a generally arcuate configuration. The draw wire includes an enlargement that passes through the final segment and engages a plurality of fingers on the final segment, which prevents the draw wire from retracting, maintaining the arcuate configuration. The segmented device can be inserted through a laparoscopic device into the intervertebral space and can be subsequently drawn into the arcuate configuration to establish the desired intervertebral spacing.

13 Claims, 3 Drawing Sheets

U.S. PATENT DOCUMENTS

| | | |
|---|---|---|
| 8,034,109 B2 * | 10/2011 | Zwirkoski .................. 623/17.11 |
| 2001/0010021 A1 | 7/2001 | Boyd et al. |
| 2004/0186481 A1 * | 9/2004 | Chern Lin et al. .............. 606/92 |
| 2006/0189999 A1 | 8/2006 | Zwirkoski |
| 2006/0265077 A1 | 11/2006 | Zwirkoski |
| 2007/0233153 A1 * | 10/2007 | Shipp et al. ..................... 606/99 |
| 2008/0125865 A1 | 5/2008 | Abdelgany |
| 2008/0208255 A1 | 8/2008 | Siegal |
| 2010/0198263 A1 * | 8/2010 | Siegal et al. .................. 606/279 |

FOREIGN PATENT DOCUMENTS

| | | |
|---|---|---|
| EP | 1925271 B1 | 8/2009 |
| WO | 0217823 A1 | 3/2002 |
| WO | 2006072941 A3 | 7/2008 |
| WO | 2008036505 A3 | 8/2008 |

* cited by examiner

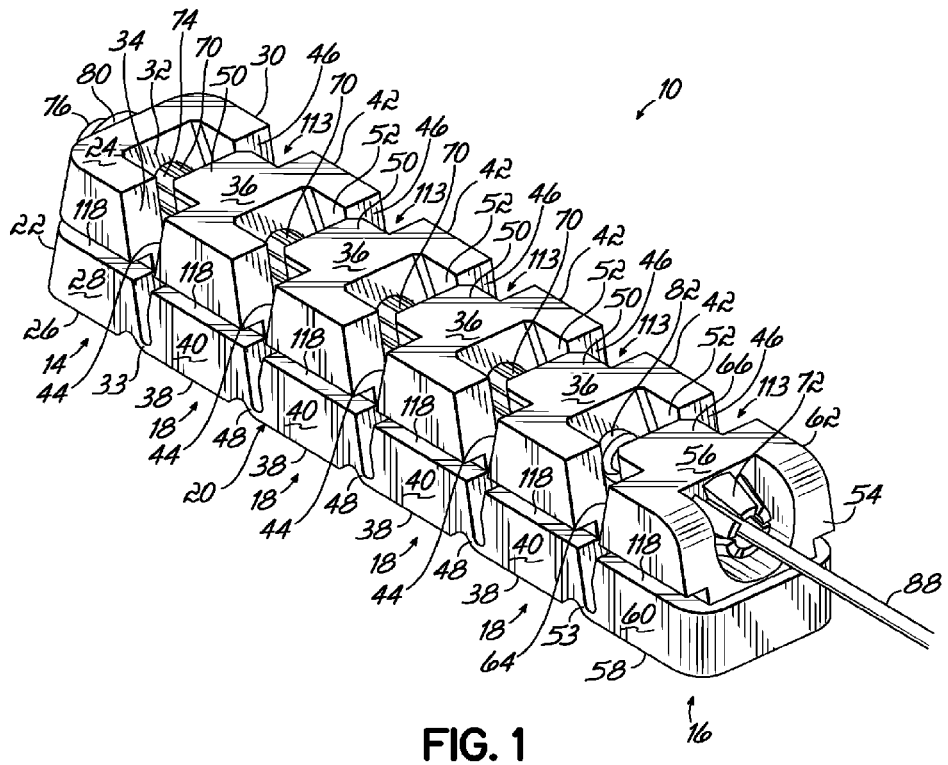

DEPLOYABLE SEGMENTED TLIF DEVICE

CROSS-REFERENCE TO RELATED APPLICATIONS

This application is a continuation of U.S. patent application Ser. No. 11/683,756, filed on Mar. 8, 2007, the entire disclosure of which is incorporated herein by reference.

BACKGROUND OF THE INVENTION

Intervertebral discs serve several functions. A primary function of the intervertebral disc is to facilitate mobility of the spine. In addition, the disc provides load bearing, load transferring, and shock absorption between vertebral discs. The disc itself is formed of two major components, a gelatinous nucleus pulposus which is surrounded by an annulus fibrosis.

The intervertebral disc can be damaged in many ways. Mechanical damage can be caused by herniation in which a portion of the nucleus projects through an opening or tear in the annulus. Progressive degeneration can be caused by either genetic or biochemical problems. In such situations, there may be a decrease in the internal nucleus volume resulting in a decrease in disc height preventing the disc from performing its designed functions.

One way to relieve the symptoms of a ruptured or deteriorated disc is by surgical removal of a portion or all of the intervertebral disc. Removal of the disc decreases disc height, which can cause a number of severe problems. Therefore, subsequent to removal of the disc, steps must be taken to restore the disc height, or separation, between the adjacent vertebrae. Many attempts have been made to insert either mechanical devices or various polymeric materials that provide solid support between the vertebrae. These devices have had varying degrees of success.

One device that has been utilized to restore disc height is shown in U.S. Pat. No. 6,387,130. The implant includes a C-shaped curve and is placed anterior within the disc space. This implant has several limitations including the use of a plurality of implants to form the curved implant, lack of a mechanism to keep the plurality of implants in plane during placement in the disc space, and lack of an instrument to effectively deliver the implant. Additionally, a number of other implants are available that due to their predetermined C-shaped profile require a significant degree of manipulation during implantation into the disc space. This manipulation may require a larger surgical access opening in the patient as well as an increased opening in the annulus of the disc.

SUMMARY OF THE INVENTION

The present invention is premised on the realization that an insert formed from a plurality of generally trapezoidal segments can be inserted between adjacent vertebrae to maintain a desired disc space. More particularly, the present invention utilizes a plurality of interconnected trapezoidal segments, which, upon insertion into a disc space, can be drawn into a generally arcuate shape within the disc space to maintain disc height. The trapezoidal segments are preferably hinged to each other. In one embodiment, a continuous strip connects the segments and provides a plurality of interconnected hinges that organize the relationship between the trapezoidal segments allowing the segments to be drawn together and to not move out of plane when creating the finalized implant shape.

The segments have a flexible wire that runs from the first or leading segment to the final trailing segment, which can be pulled or moved relative to the trapezoidal segments to draw the segments together into a generally arcuate shape. A locking mechanism is provided to prevent the trapezoidal segments from separating from each other, maintaining the generally arcuate shape.

The flexible wire preferably includes a breakaway section. Force on the wire will first act to bend the insert into an arcuate shape and lock it into position. Additional force will cause the upstream portion of the wire to break away, allowing it to be removed.

The objects and advantages of the present invention will be further appreciated in light of the following detailed description and drawings in which:

BRIEF DESCRIPTION OF THE DRAWING

FIG. 1 is a perspective view of the present invention;

FIG. 2 is a cross sectional depiction of the implant shown in FIG. 1 prior to deployment;

DETAILED DESCRIPTION

Figure 7:
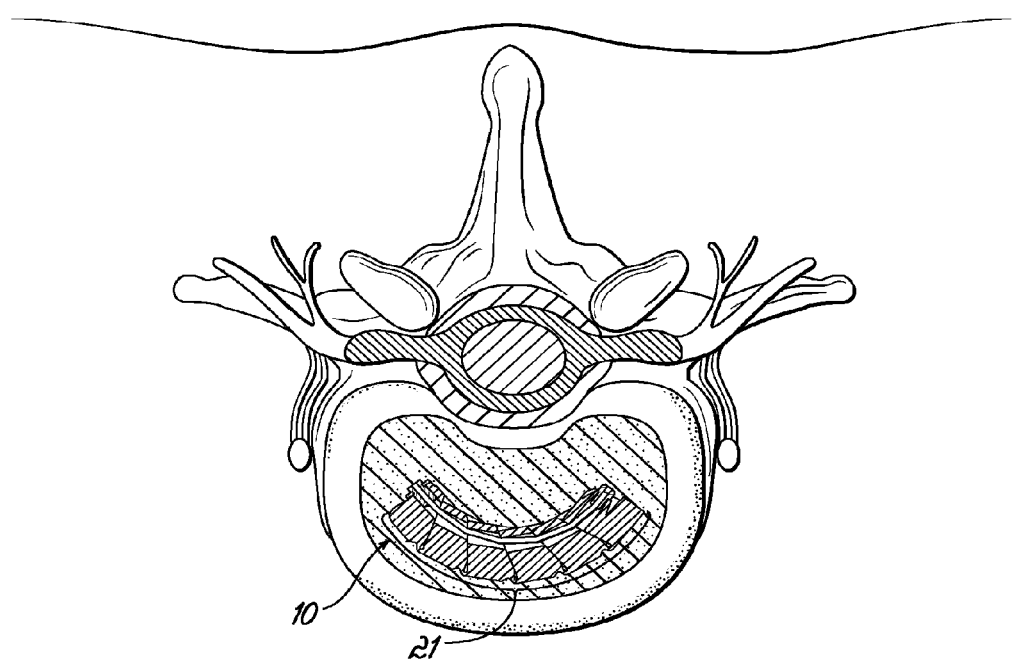
FIG. 7 is a diagrammatic cross sectional view of the device shown in FIG. 1 in an implanted state.

The present invention is an intervertebral support 10 that is designed to be implanted within the intervertebral space between adjacent vertebrae. The support 10 includes a leading segment 14, a terminal segment 16 and a plurality of intermediate segments 18. In one embodiment, four intermediate segments are included. In other embodiments, more or less intermediate segments can be utilized depending on factors such as patient anatomy or implant positioning. The segments 14,16 and 18 are connected together by a continuous connective portion 20 along the base of the segments 14, 16 and 18 that following implantation forms an anterior wall 21 of the implant (FIG. 7).

The leading segment 14 includes a rounded leading end 22, radially inner side 24, radially outer side 26, and mirror image top 28 and bottom 30 sides. The leading segment 14 can optionally be configured to have a tapered or wedge shaped leading end 22 to facilitate implantation. The terms "radially inward", "radially outward", "top" and "bottom" reference the implanted support 10. Segment 14 further includes an internal side 34, which is tapered inwardly and includes a notch 32. Segment 14 is connected at a hinge 35 to the next intermediate segment 18.

Each of the intermediate segments 18 are identical. As shown, the intermediate segments 18 include a radially inner side 36, a radially outer side 38, a top surface 40 and a bottom surface 42, and inner walls 44 and 46. Wall 46 connects to the next adjacent intermediate segment by a hinge 48. The inner walls 44 and 46 narrow as they extend from the outer side 38 towards the inner side 36 forming a generally trapezoidal cross section. The inner wall 44 further includes a key 50, which is adapted to reside within the notch 32 of the leading segment 14 Inner wall 46 includes a notch 52, which is adapted to receive the key 50 of the next adjacent intermediate segment.

The trailing segment 16, is connected to intermediate segment 18 by a hinge 53, and includes a trailing end 54, a radially inner side 56 and a radially outer side 58, as well as a top surface 60 and a bottom surface 62. The inner wall 64 of segment 16 is tapered inwardly from the outer side 58 towards the inner side 56. This inner wall 64 further includes a key 66 adapted to fit within a notch 52 of intermediate segment 18.

All of the segments include a central channel 70 that extends from leading end 22 to trailing end 54. A plurality of inwardly biased fingers 72 surround the terminal end 73 of channel 70.

Draw wire 74 extends through channel 70 and includes a distal knob 76, having a lock ring 80 positioned within a channel in knob 76. This prevents the knob 76 from moving through channel 70. Draw wire 74 extends to a proximal bead 82 and is swedged into a narrow end 84. Bead 82 further includes a larger end 86. A tensioning line 88 is swedged to this larger end 86.

Bead 82 includes a shoulder 89 between its narrow end 84 and larger diameter end 86. This shoulder 89 is designed to engage the proximal ends of fingers 72 and prevent the draw wire 74 from retracting into channel 70.

In order to enable the tensioning line to separate from bead 82, the draw wire 74 is swedged more tightly to bead 82 than is tensioning line 88. Preferably, the draw wire 74 will be swedged on bead 82 with 90 pounds of force, whereas the tensioning line 88 will be swedged onto end 84 with only about 20-30 pounds of force. Thus, increasing force applied to tensioning line 88 will eventually cause it to separate from bead 82, leaving draw wire 74 in position within device 10.

The support 10 is preferably made from any material that has been approved by the Food and Drug Administration for use in spinal applications. One preferred material is a polymeric material, such as polyether ether ketone (PEEK). Any material that has adequate strength and flexibility as well as compatibility for this intended application may be used.

Figures 3, 4, 5:
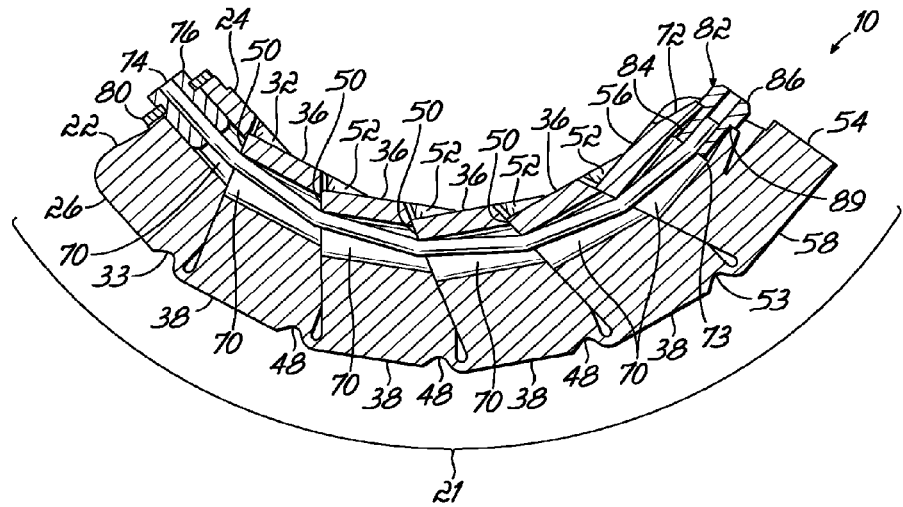
FIG. 3 is a cross sectional view of the implant shown in FIG. 1 in a deployed position.
FIG. 4 is a perspective view partially broken away of an apparatus used to apply the insert shown in FIG. 1.
FIG. 5 is a cross sectional view taken at lines 5-5 of FIG. 4.
Figure 6:
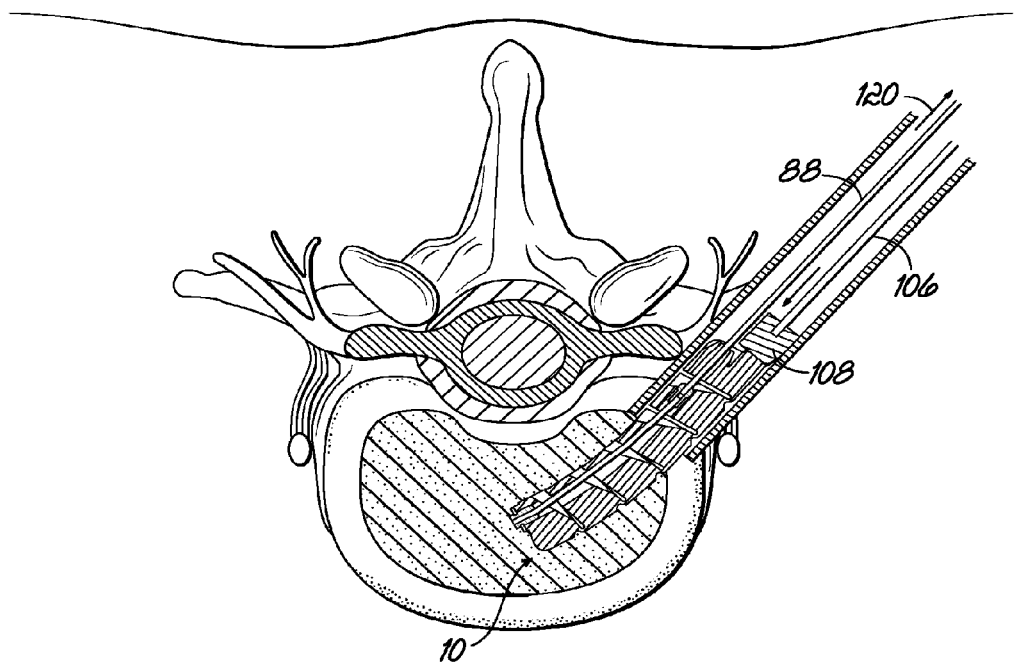
FIG. 6 is a cross sectional diagrammatic view showing the implantation of the device shown in FIG. 1.

As shown more particularly in FIGS. 5, 6 and 7, the support 10 is inserted into the intervertebral space through an opening created in the annulus of the intervertebral disk using an applicator 100. Applicator 100 includes a rectangular barrel 102 fixed to a handle member 104. Applicator 100 further includes a rod 106 having a plunger 108 at one end and a knob 110 at the opposite end. Rod 106 can be advanced down the barrel 102 by pressing trigger 111 of handle 112. The tensioning line 88 extends through the barrel 102, around a tensioning spool 114 to maintain the desired tension on draw wire 74. A sufficient length of line 88 is on spool 114 to allow the support 10 to be inserted into the intervertebral space. The end of line 88 (not shown) is fixed to the spool 114. Tensioning spool 114 either has a preset resistance to inhibit rotation, or a screw type mechanism 122 to tighten spool 114. A tensioning spring can also be employed.

As shown in FIG. 5, the barrel 102 further includes inner ridges 116. The upper and lower walls of the segments 14,16 and 18 include channels 118 and 120, which are adapted to ride on ridges 116 in barrel 102 maintaining the support in a linear position while in barrel 102.

To insert the support 10 of the present invention, the intervertebral space in the cervical, thoracic, or lumbar region of the spine is accessed by way of an incision through the patient's tissue that leads to the vertebral column. Preferably, the vertebral column is accessed from a transforaminal approach. Alternatively, the vertebral column can be accessed through a lateral, anterior, anterior-lateral, posterior or posterior-lateral approach. The vertebral space is surgically prepared as desired, removing all or some of the nucleus or annulus fibrosis to provide any necessary spacing for the support 10. Proper incisions are performed to allow the support to pass to and through the annulus fibrosis to the intervertebral space.

Support 10 is then placed into the disc space. It can be advanced using the handle 111 to move tab 128, rod 106 and plunger 108 through barrel 104. This moves support 10 out barrel 104 into the intervertebral space. Alternately, rear knob 110 can be struck with a hammer or similar instrument to provide the necessary force to move the support 10 into the disc space. Spring biased tab 124 prevents the rod 106 from moving in the opposite direction.

As the support 10 is inserted into the space, tension is applied in the direction of arrow 120, which causes the support 10 to rotate into a generally arcuate or arched position. The radial continuity of the arch, as well as the degree of curvature can vary as desired. Generally, the support 10 will assume a general curved shape. The support 10 can be predisposed to have the general curved shape prior to loading into the applicator 100. Alternatively, the support 10 can be linear prior to loading into the application 100 and the generally curved shape can be achieved through actuation of the applicator 100.

Once the support 10 is properly inserted, tensioning line 88 is fixed and increased force is applied by plunger 108 against the rear surface 54 of the support 10. The applied force will exceed the force holding the tensioning line 88 to the rear portion of bead 82, separating the tensioning wire 88 from bead 82 and allowing the tensioning line 88 to be withdrawn.

More particularly, as the support 10 is inserted into the disc space, the tension on line 88 will cause the adjacent segments to rotate about the hinges and close the gap 113 between the adjacent segments. In one embodiment, the gap 113 has a generally triangular shape. Alternatively, the gap can be of any shape to accommodate movement of the segments in a manner that creates a desired implantation shape of the implantation shape of the implant, such as an arcuate shaped implant (C-shaped or V-shaped). This will continue until the support transforms from a linear shape and assumes the configuration shown in FIG. 3. As the support 10 changes to this final shape, the enlarged portion of bead 82 will pass through channel 70 and through the fingers 72. The fingers 72 expand as the enlarged portion 86 of bead 82 passes through. The fingers 72 then retract, engaging the shoulder 89 between the narrow inner portion 84 of bead 82 and the larger end 86 (see FIG. 3). This will prevent the wire 74 from moving in a direction opposite arrow 120 and permanently lock the support 10 in a generally arcuate position.

The implanted support 10 provides needed support between adjacent vertebrae. The interlocking notch and key configuration of the different segments prevents the adjacent segments from rotating relative to each other providing vertical stability.

The present invention can be modified in a number of ways, as desired. In particular, the connection portion 20 can be removed, and the individual segments connected by a hinge pin mechanism so that the individual segments are formed separately but attached together prior to implantation. Additionally, surfaces of the implant can be modified to have projections or teeth that provide friction between the implant and patient anatomy. Further, the support can be formed from any material that is suitable for implantation and possesses the required strength.

This support structure of the present invention provides many different advantages. It enables a support to be located into the intervertebral area utilizing a minimally invasive surgical procedure. This is particularly beneficial because of the limited space available in such a surgical procedure. Further, forcing the device into the intervertebral space as tension is applied causes the structure to bend as it passes into the intervertebral space, again allowing a longer support device to be inserted into the space. Further, the draw wire with the locking bead mechanism maintains this in a permanently arcuate condition. Finally, the interlocking notch and key structure of the adjacent segments prevent relative rotation of the segments about their central axis.

This has been a description of the present invention along with the preferred method of practicing the present invention. However, the invention itself should only be defined by the appended claims.

What is claimed:

1. A system for inserting an interbody fusion support through a foramen into an intervertebral space comprising:
    an interbody fusion support having a plurality of segments configured to be moved into a curved position, the support further comprising a draw wire; and
    an apparatus for inserting the support, the apparatus including
        a handle;
        a linear barrel connected to the handle and adapted to receive said support;
        a plunger configured to be inserted through said barrel and apply force to said support to move the support in a first direction; and
        a tensioner connected to the handle and configured to be inserted through said barrel and to apply force on said draw wire in a second direction as said support moves in said first direction, wherein said tensioner is removably attached to said support, wherein said plunger and said tensioner are configured to operate at the same time within the barrel to advance said support through said barrel and into the intervertebral space.

2. The system of claim 1, wherein said first and second directions are opposite.

3. The system of claim 1, wherein said tensioner includes a spool and a tensioning line removably attached to said draw wire, the spool receiving the tensioning line, wherein the tensioning line is configured to be inserted through said barrel.

4. The system of claim 1, wherein the barrel includes inner ridges configured to maintain said support in a linear position as the support moves through the barrel.

5. The system of claim 1, wherein the apparatus further comprises a biased tab configured to prevent the plunger from moving in the second direction.

6. A method of inserting an interbody fusion support into an intervertebral space, the method comprising:
    providing a linear support having a plurality of segments, the plurality of segments including a leading segment and a trailing segment, the linear support configured to be moved into a curved position;
    providing an inserter comprising a handle, a linear barrel connected to the handle and configured to receive said support, a plunger configured to be inserted through said barrel and move said support in a first direction, and a tensioner connected to the handle, the tensioner including a tensioning line, the tensioner configured to apply tension on said tensioning line in a second direction opposite the first direction, wherein said plunger and said tensioning line are configured to operate at the same time within the barrel to advance said support through said barrel and into the intervertebral space;
    inserting said linear support into said barrel and removably attaching said tensioning line to said support;
    moving said linear support in said first direction with said plunger, leading segment first, through a surgical opening into said intervertebral space while applying tension on said tensioning line in said second direction, forcing said support to curl into the curved position as said support enters said intervertebral space;
    applying tension on said tensioning line until a locking element engages the trailing segment of the support; and
    removing said tensioning line by applying additional force on the tensioning line, wherein the locking element prevents the support from moving from the curved position to a linear position when the tensioning line is removed.

7. The method of claim 6, further comprising the step of maintaining a planar connection between the segments when applying tension on the tensioning line.

8. The method of claim 7, further comprising the step of providing a key and notch relationship between adjacent segments to maintain the planar connection between the adjacent segments.

9. The method of claim 7, further comprising the step of providing a connection portion on the support to maintain the planar connection between segments.

10. The method of claim 6, wherein applying tension includes applying a first amount of tension on the tensioning line and wherein removing the tensioning line includes applying a second amount of tension on the tensioning line to separate the tensioning line from the support, wherein the second amount of tension is greater than the first amount of tension.

11. The method of claim 6, wherein the linear support has a draw member fixed to the leading segment, extending through the plurality of segments and releasably attached to the tensioning line, wherein the locking element includes a first locking element disposed on the draw member and a second locking element disposed on the trailing segment, wherein applying tension includes applying tension on the tensioning line to curl the support until the first locking element moves through the trailing segment and engages the second locking element on the trailing segment.

12. The method of claim 11, wherein the first locking element includes a bead and the second locking element includes a plurality of flexible fingers on the trailing segment, wherein applying tension includes moving the bead through the trailing segment which thereby opens the fingers, and allowing the fingers to close behind the bead when the bead passes through the fingers, preventing the support from moving back to the linear position.

13. The method of claim 6, wherein the step of providing a linear support having a plurality of segments includes connecting a plurality of separate segments.

* * * * *